US011298270B2

(12) United States Patent
Knox

(10) Patent No.: US 11,298,270 B2
(45) Date of Patent: Apr. 12, 2022

(54) COLLAPSIBLE MENSTRUAL CUP

(71) Applicant: Chante Knox, Atlanta, GA (US)

(72) Inventor: Chante Knox, Atlanta, GA (US)

( * ) Notice: Subject to any disclaimer, the term of this patent is extended or adjusted under 35 U.S.C. 154(b) by 196 days.

(21) Appl. No.: 16/841,893

(22) Filed: Apr. 7, 2020

(65) Prior Publication Data

US 2021/0307971 A1 Oct. 7, 2021

(51) Int. Cl.
*A61F 13/20* (2006.01)
*A61F 13/45* (2006.01)
*A61F 13/53* (2006.01)
*A61F 13/26* (2006.01)

(52) U.S. Cl.
CPC ...... *A61F 13/2045* (2013.01); *A61F 13/2051* (2013.01); *A61F 13/26* (2013.01); *A61F 13/53* (2013.01); *A61F 2013/4562* (2013.01)

(58) Field of Classification Search
CPC .......... A61F 13/2045; A61F 2013/4562; A61F 13/2051
See application file for complete search history.

(56) References Cited

U.S. PATENT DOCUMENTS

| | | | |
|---|---|---|---|
| 3,128,767 A | 4/1964 | Nolan | |
| 3,216,422 A * | 11/1965 | Steiger | A61F 6/08 604/330 |
| 4,630,602 A * | 12/1986 | Strickman | A61F 6/08 128/837 |
| 5,295,984 A | 3/1994 | Contente et al. | |
| 5,476,455 A * | 12/1995 | Silber | A61F 5/4553 604/330 |
| 5,947,992 A | 9/1999 | Zadini et al. | |
| 6,126,616 A | 10/2000 | Sanyal | |
| 6,264,638 B1 | 6/2001 | Contente | |
| 6,796,973 B1 | 9/2004 | Contente et al. | |
| D760,897 S | 7/2016 | Teo | |
| 10,016,308 B2 | 7/2018 | Knox | |
| D837,980 S | 1/2019 | Sedic | |
| D841,808 S | 2/2019 | Drach | |
| D852,361 S | 6/2019 | Sedic | |
| D852,362 S | 6/2019 | Sedic | |
| D864,390 S | 10/2019 | Sedic | |
| 2008/0200888 A1 | 8/2008 | Gooch et al. | |
| 2010/0312204 A1 | 12/2010 | Sheu | |
| 2016/0193089 A1 * | 7/2016 | Edmunds | A61F 13/208 600/572 |
| 2019/0000680 A1 * | 1/2019 | DeOliveira | A61F 13/2037 |

\* cited by examiner

*Primary Examiner* — Susan S Su
(74) *Attorney, Agent, or Firm* — Larson & Larson, P.A.; Justin P. Miller; Frank Liebenow

(57) ABSTRACT

The collapsible menstrual cup prevents spillage by absorbing menstrual fluids. Separating the absorbent elements into discrete pieces allows for a nested, collapsed, flat state, and an expanded, separated state. Discrete pieces being individual elements able to move with respect to each other, in contrast to a unified layer of material that would fold when moved from a flat shape to a cupped shape. Thus, storing multiple devices on one's person is simplified without compromising functionality. The absorbent elements are shaped like flower petals, radiating outward from a central point. At the center is an optional central absorbent element. In the collapsed position the absorbent elements take positions in close proximity, nesting next to each other. In the expanded position for use, the absorbent elements spread out, allowing the reservoir to expand, preparing for use.

14 Claims, 11 Drawing Sheets

COLLAPSIBLE MENSTRUAL CUP

FIELD

The described device relates to feminine hygiene products, specifically to those that collect vaginal menstrual discharge.

BACKGROUND

Devices for the absorption of menstrual discharge are known in the art, all seeking to solve the issue of discretely collecting menstrual blood. But the known devices each present significant drawbacks.

Sanitary napkins are bulky and prone to leakage. Tampons are a less-bulky alternative, but due to direct contact with the inner surfaces of the vaginal canal, the tampon absorbs all the fluids of the vagina. The complete absorption affects the natural moisture balance of the vaginal canal, in severe cases resulting in toxic shock syndrome.

What is needed is a device that provides for the sanitary disposal of menstrual fluids without the risks of the prior art.

SUMMARY

The collapsible menstrual cup prevents spillage by absorbing menstrual fluids. Separating the absorbent elements into discrete pieces allows for a nested, collapsed, flat state, and an expanded, separated state. Discrete pieces being individual elements able to move with respect to each other, in contrast to a unified layer of material that would fold or stretch when moved from a flat shape to a cupped shape.

Thus, storing multiple devices on one's person is simplified without compromising functionality.

The absorbent elements are shaped like flower petals, radiating outward from a central point. At the center is an optional central absorbent element.

In the collapsed position the absorbent elements take positions in close proximity, nesting next to each other.

In the expanded position for use, the absorbent elements spread out. This allows the reservoir to expand and prepare for use.

In an alternative embodiment, the absorbent elements are formed from a single sheet of material, with sections of the material removed to create separation between sections of absorbent material. Thus, the remaining portions of material can freely move toward and away from each other without being hindered by intervening material.

The absorbent elements are formed from a hydrophilic material, or a material attracted to water. The volume of hydrophilic material is selected to absorb around eighteen grams of menstrual fluid—equivalent or greater than the most absorbent available tampons.

The absorbent elements are held in position by being sandwiched between two membranes: an outer impermeable membrane and an inner semi-permeable membrane.

The outer impermeable membrane prevents any non-absorbed menstrual fluids from leaking out of the device. For example, if the device is worn beyond the capacity of the absorbent elements to trap liquids.

The inner semi-permeable membrane includes regular, spaced penetrations to direct menstrual fluids to the absorbent elements. The inner layer may also be a permeable material, such as a mesh or a wicking cotton material, rather than a perforated impermeable material.

The two layers are sealed—by plastic welding, adhesive, or similar—around the absorbent elements, creating pockets. The sealing prevents rubbing between the layers, thus preventing noise. Given that the device will be used in public restrooms, this creates a quiet device that the user can unwrap and insert discreetly.

As a variation to the disclosed design, the absorbent elements may be distributed in a honeycomb pattern. The absorbent elements would still include a collapsed position with close spacing and an expanded position with increased spacing.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Figure 1:
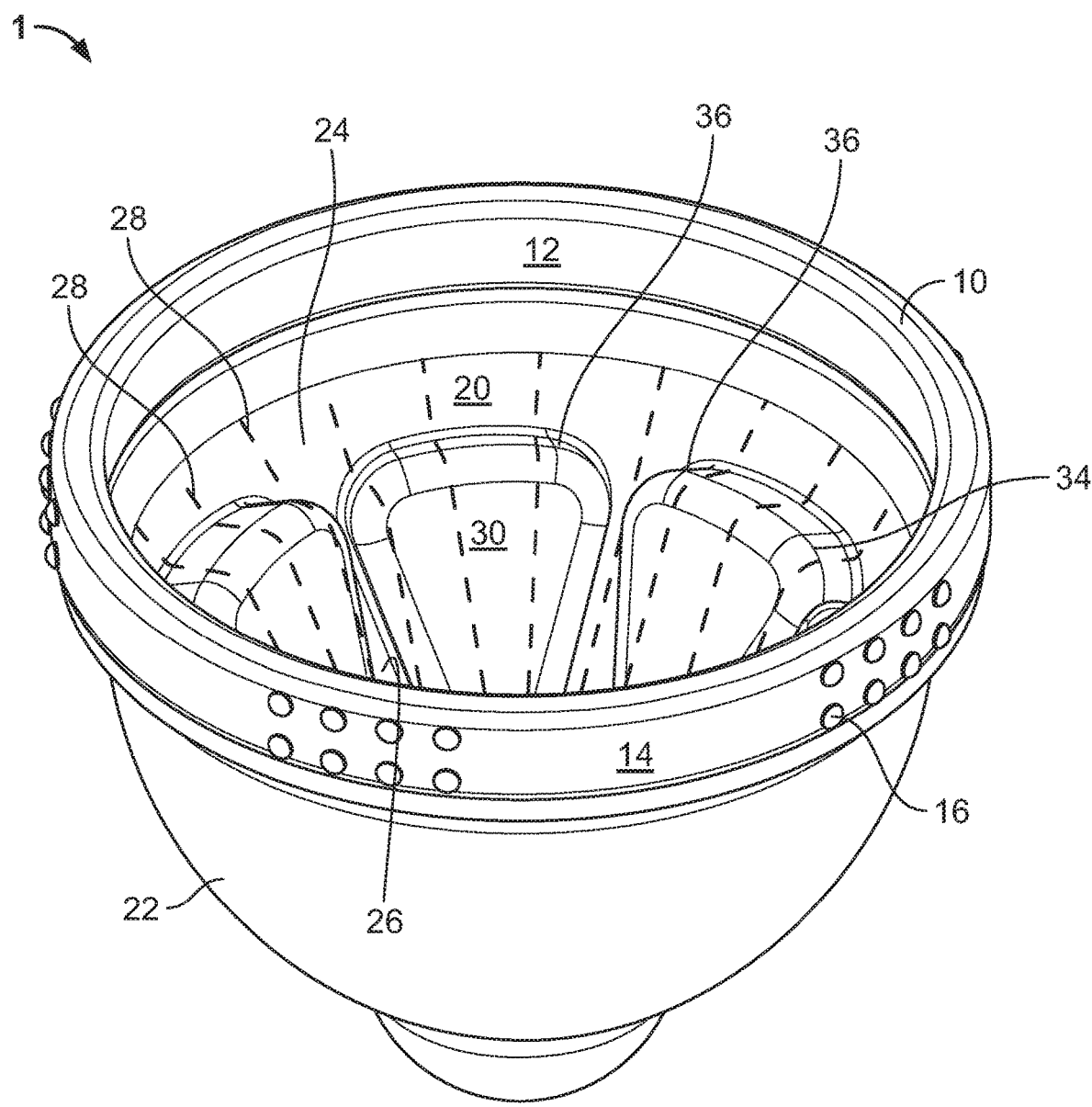
FIG. 1 illustrates a first isometric view of the collapsible menstrual cup.
Figure 2:
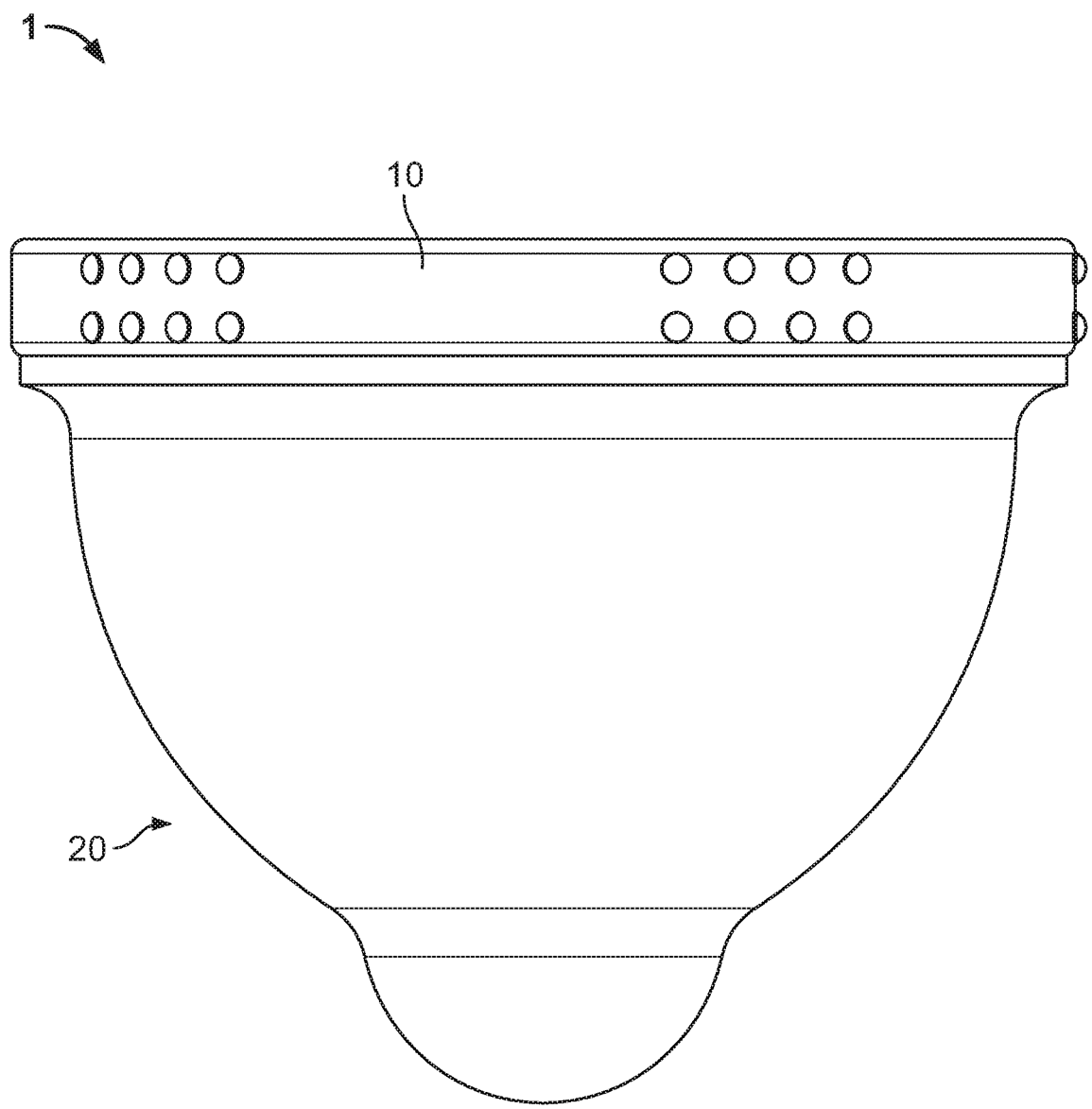
FIG. 2 illustrates a first side view of the collapsible menstrual cup.
Figure 3:
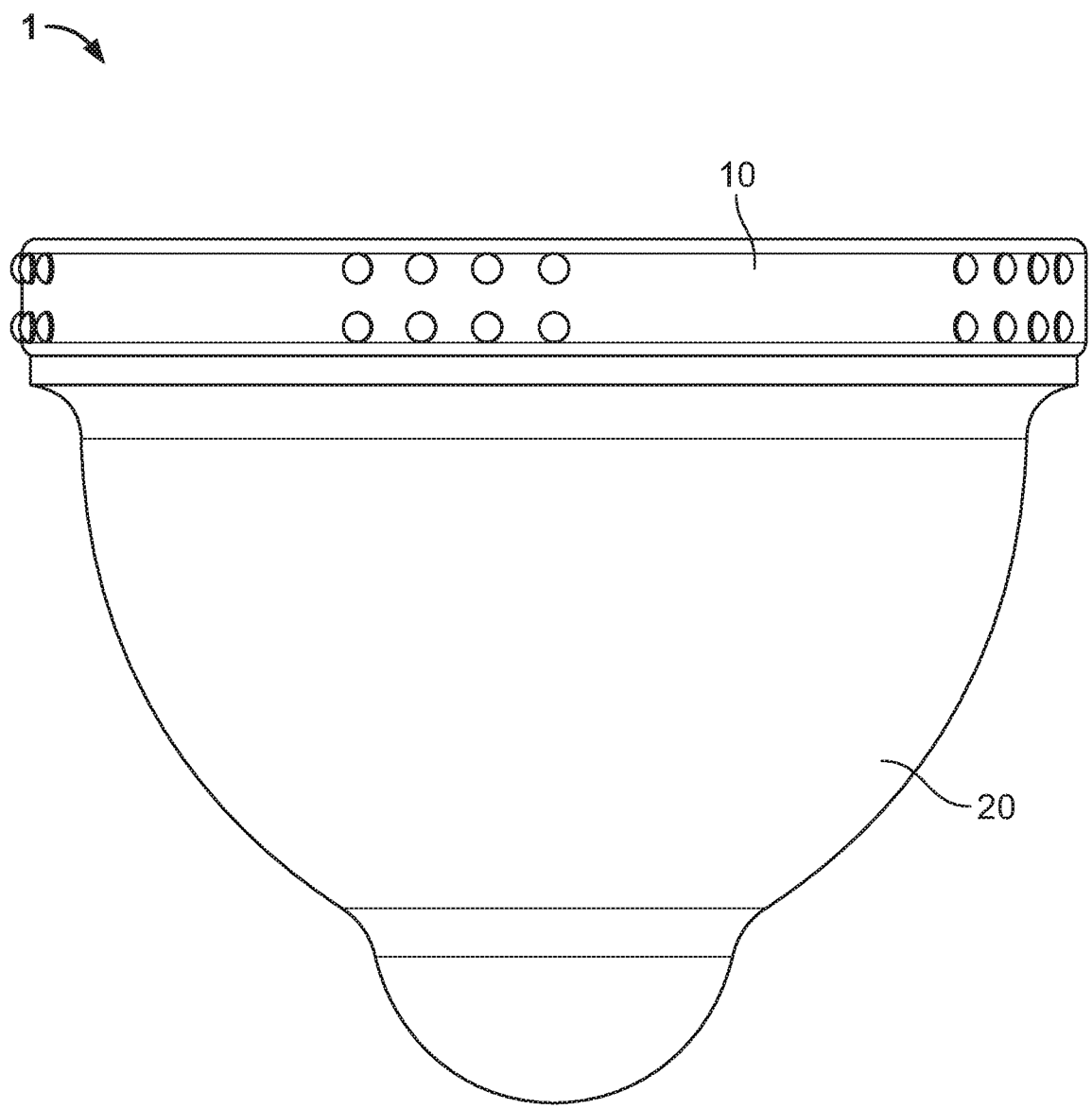
FIG. 3 illustrates a second side view of the collapsible menstrual cup.
Figure 4:
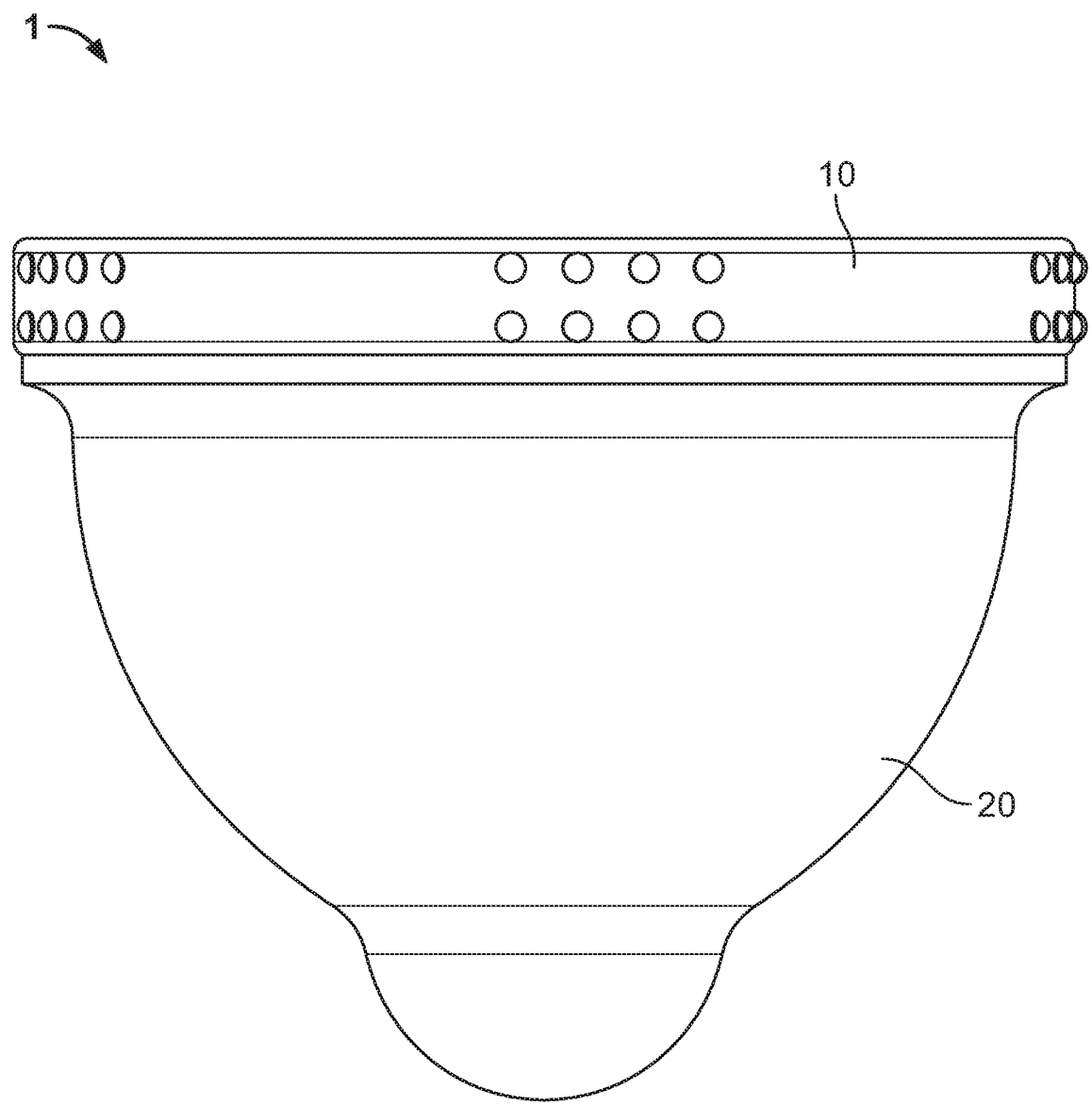
FIG. 4 illustrates a third side view of the collapsible menstrual cup.
Figure 5:
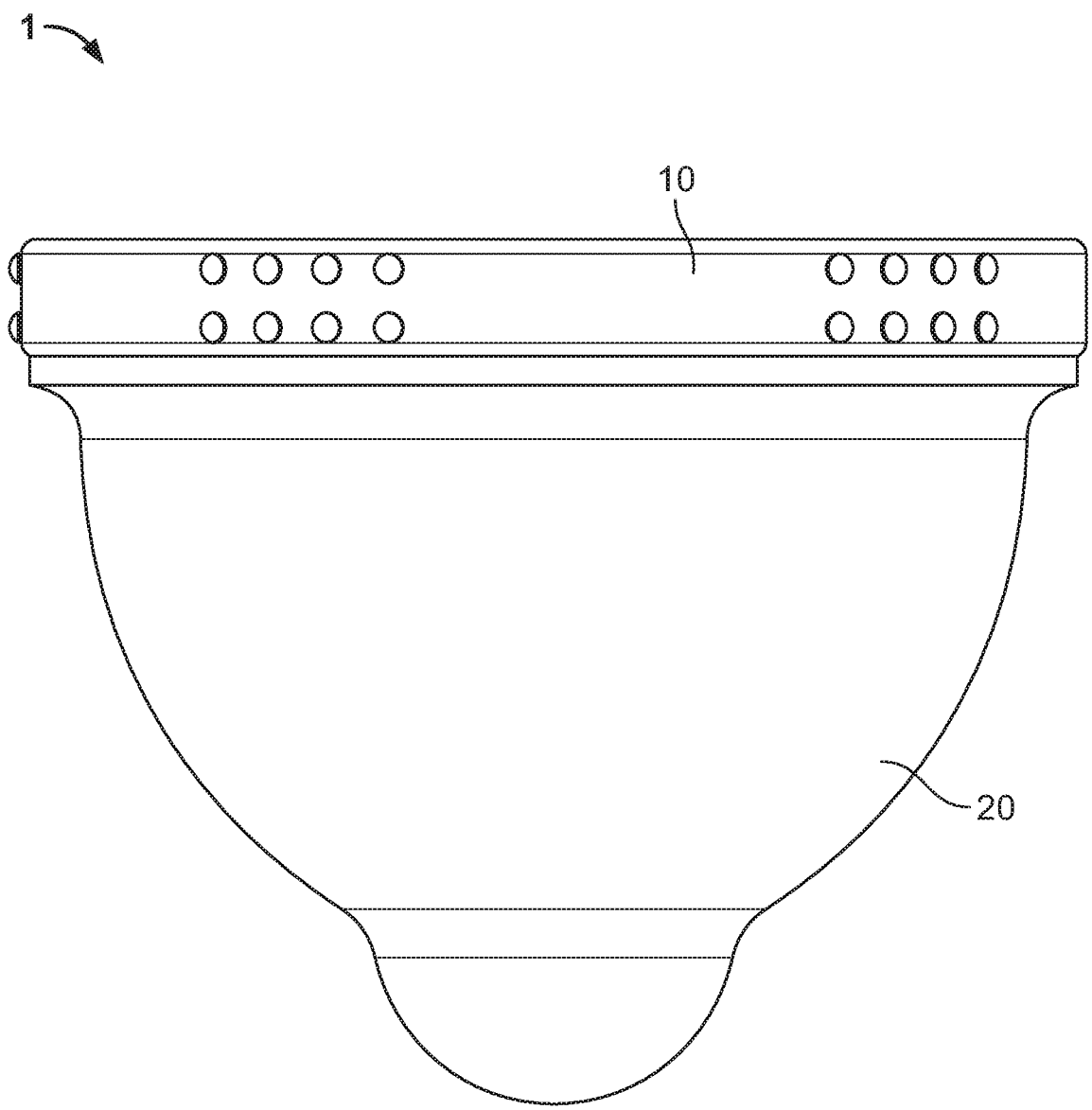
FIG. 5 illustrates a fourth side view of the collapsible menstrual cup.

Reference will now be made in detail to the presently preferred embodiments of the invention, examples of which are illustrated in the accompanying drawings. Throughout the following detailed description, the same reference numerals refer to the same elements in all figures.

Referring to FIG. 1, a first isometric view of the collapsible menstrual cup is shown.

The collapsible menstrual cup 1 includes a rim 10 formed from a rim inner surface 12 and rim outer surface 14, with optional rim outer projections 16.

The reservoir 20 is formed from an exterior barrier 22 and an interior barrier 24. The exterior barrier 22 and interior barrier 24 are affixed to each other with a layer weld 26, thus creating a unified interior/exterior barrier 22/24 in any location where the barriers 22/24 are not separated by absorbent material 30 (location of which is marked in FIG. 1 as would be seen behind the interior barrier 24, see also FIGS. 8 and 9).

Perforations 28 allow menstrual fluid to pass through the interior barrier 24 and into the absorbent material 30.

The absorbent material 30 includes central segment 32 (see FIG. 8) and discrete segments 34. The absorbent material sits within pockets 36 where the exterior barrier 22 and interior barrier 24 are separated. The layer welds 26 surround the pockets 36, holding the absorbent materials 30 in position.

Referring to FIGS. 2, 3, 4, and 5, multiple side views of the collapsible menstrual cup are shown.

The collapsible menstrual cup 1 includes a rim 10 affixed to a reservoir 20.

Figure 6:
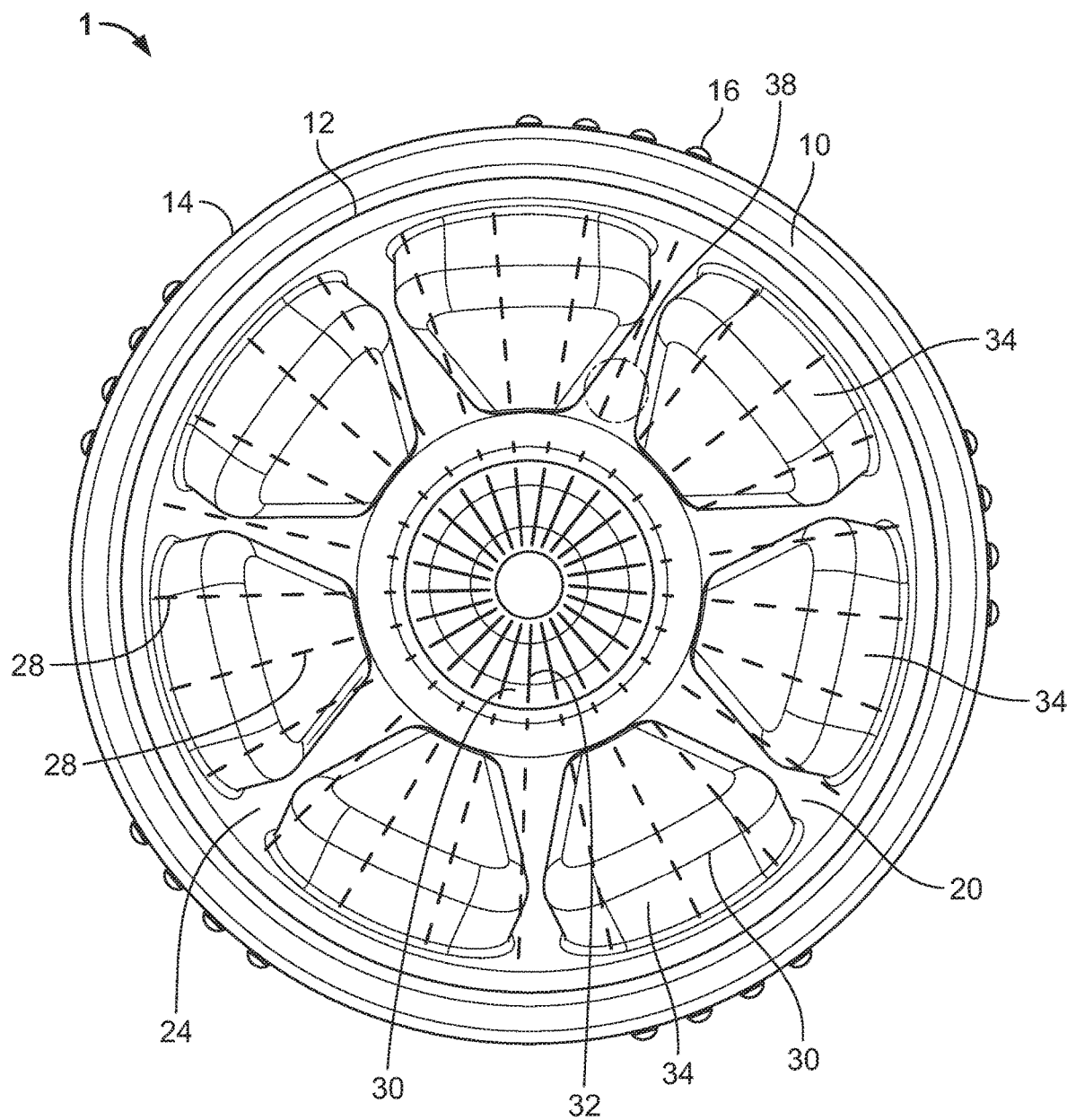
FIG. 6 illustrates a top view of the collapsible menstrual cup.

Referring to FIG. 6, a top view of the collapsible menstrual cup is shown.

Again shown is the reservoir 20, with the interior barrier 24 permitting passage of fluids through perforations 28 to the absorbent material 30 formed from central segment 32 and discrete segments 34.

Note that this figure shows the collapsible menstrual cup 1 in an expanded position, resulting in segment separation 38 between the discrete segments 34. In particular, the discrete segments 34 are separated near the central segment 32, where the most expansion is required to open the collapsible menstrual cup 1.

Figure 7:
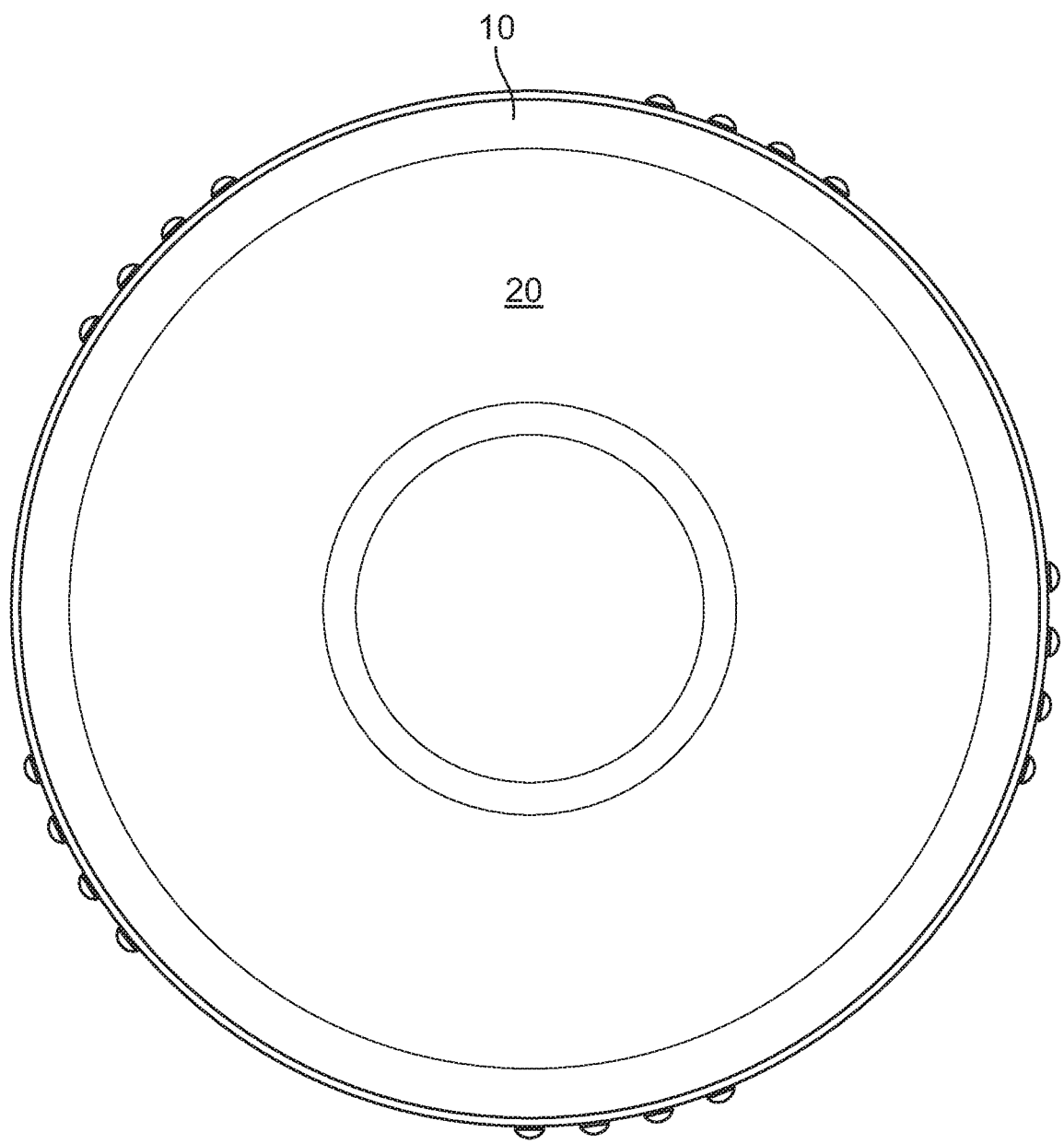
FIG. 7 illustrates a bottom view of the collapsible menstrual cup.

Referring to FIG. 7, a bottom view of the collapsible menstrual cup is shown.

The rim 10 and reservoir 20 are visible.

Figure 8:
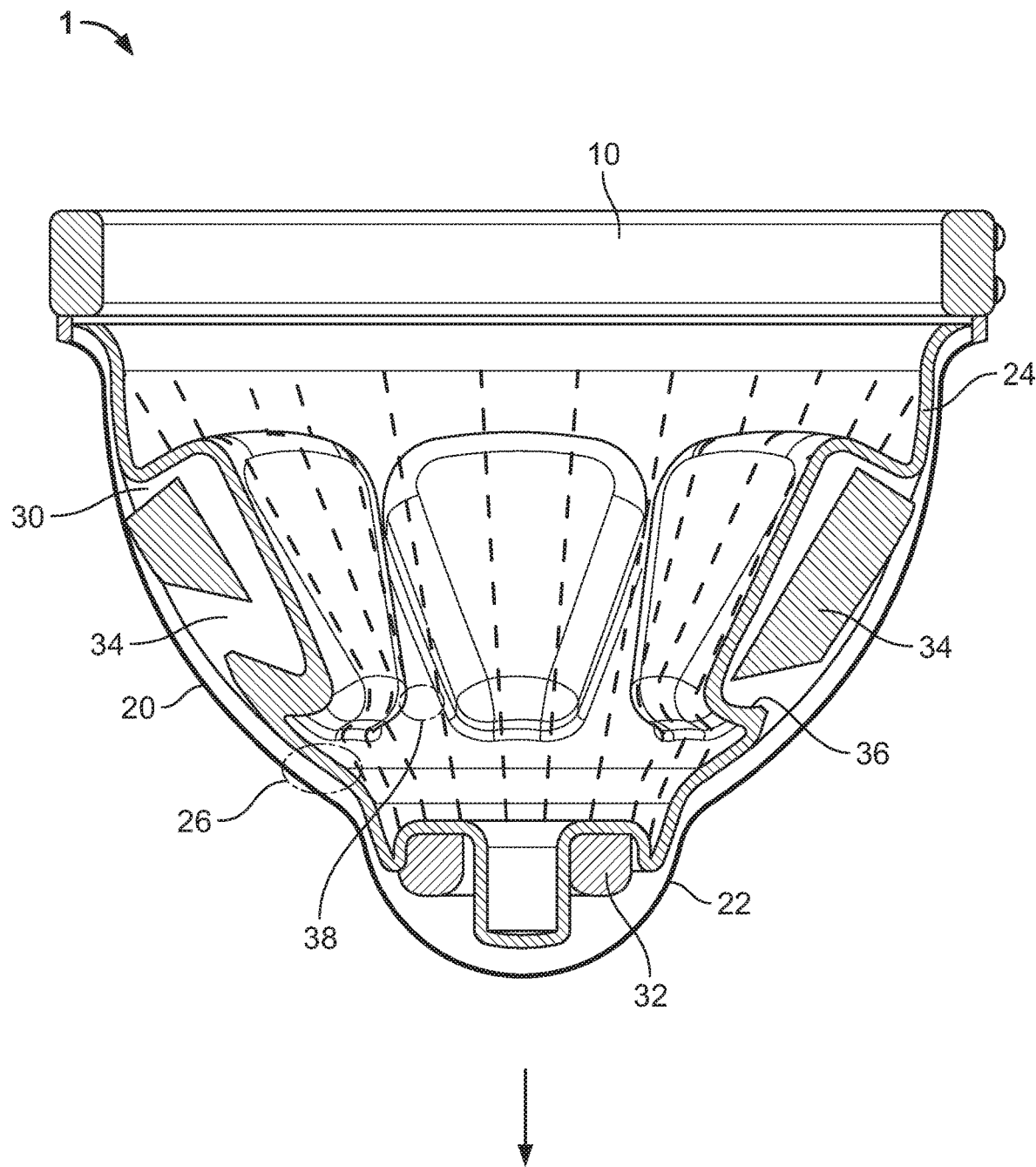
FIG. 8 illustrates a cross-sectional view of the collapsible menstrual cup.

Referring to FIG. 8, a cross-sectional view of the collapsible menstrual cup is shown.

The reservoir 20 is shown formed from an exterior barrier 22 and an interior barrier 24, joined at layer welds 26.

The absorbent material 30 includes central segment 32 and discrete segments 34 within pockets 36.

Segment separation 38 is again visible between discrete segments 34, which separate when the menstrual cup is opened downward, as shown by the arrow.

Figure 9:
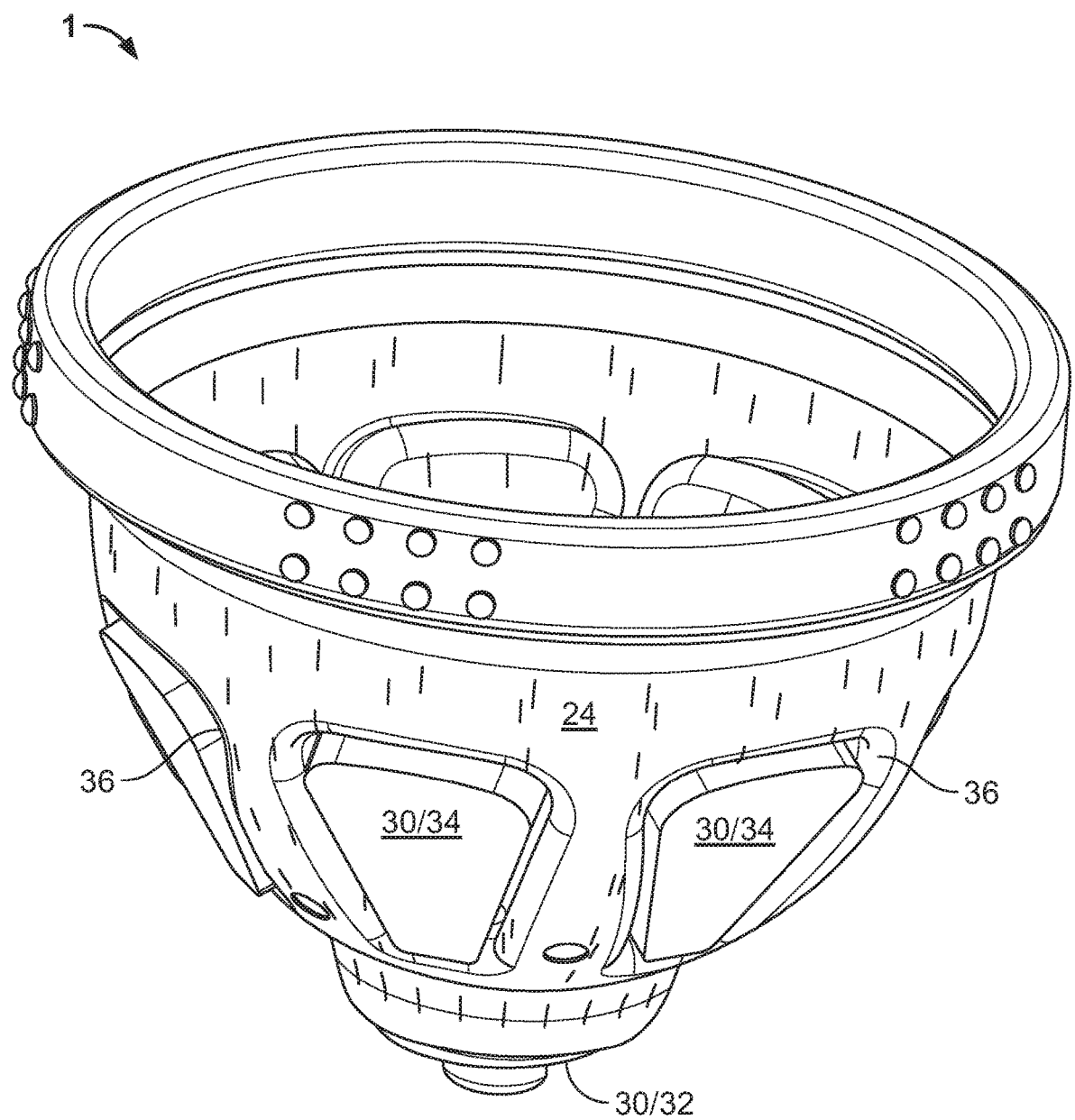
FIG. 9 illustrates a second isometric view with the outside layer hidden of the collapsible menstrual cup.

Referring to FIG. 9, a second isometric view with the outside layer hidden of the collapsible menstrual cup is shown.

The interior barrier 24 is shown with pockets 36 formed to hold the absorbent material 30 comprising central segment 32 and discrete segments 34.

Figure 10:
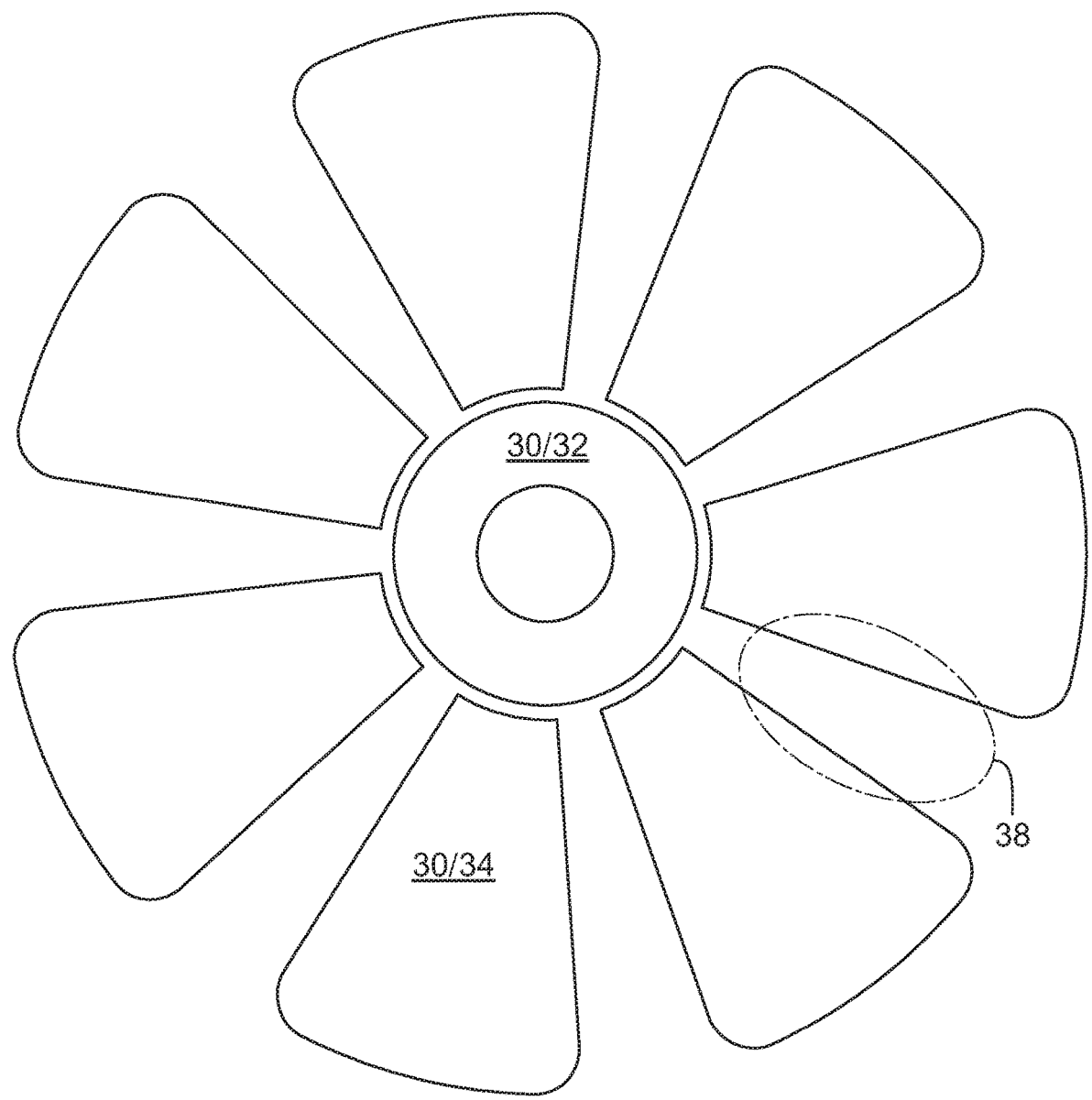
FIG. 10 illustrates a view of the absorbent elements of the collapsible menstrual cup.

Referring to FIG. 10, a view of the absorbent elements of the collapsible menstrual cup is shown.

The absorbent material 30 of the central segment 32 and discrete segments 34 is shown in a collapsed position. Note the consistent segment separation 38.

Figure 11:
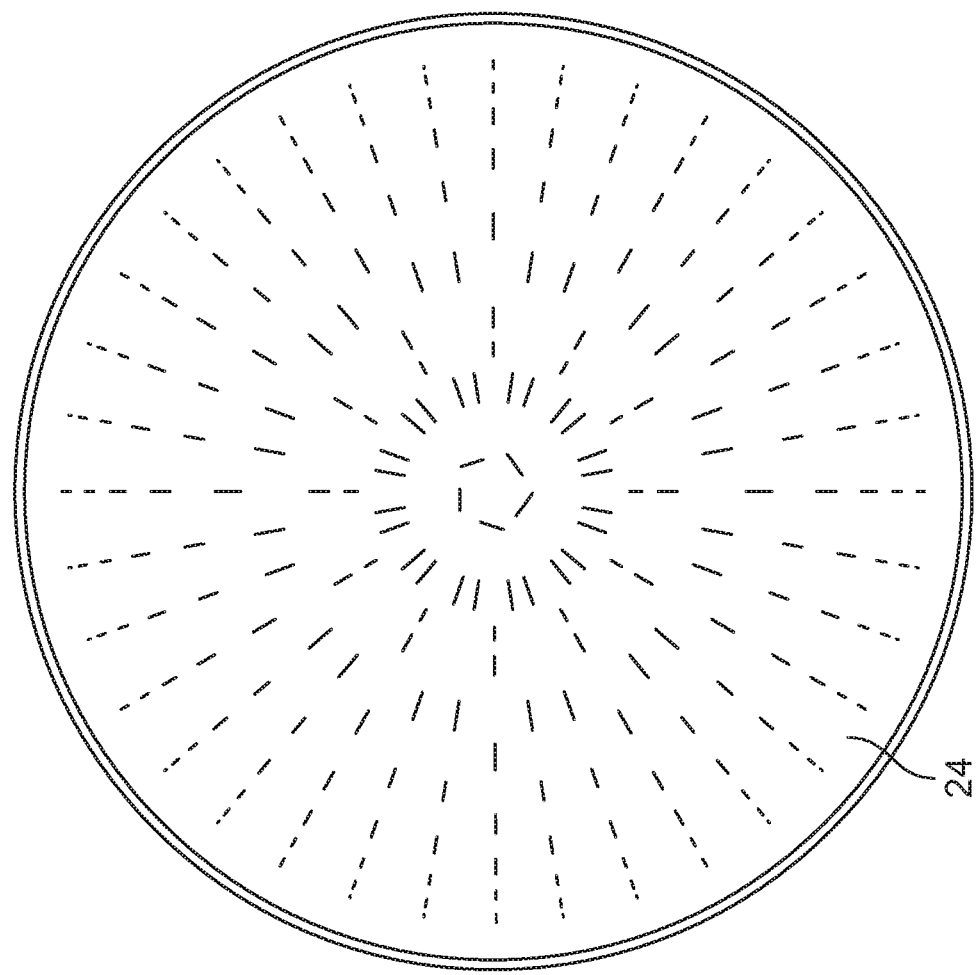
FIG. 11 illustrates a view of the outer layer of the collapsible menstrual cup.
Figure 11:
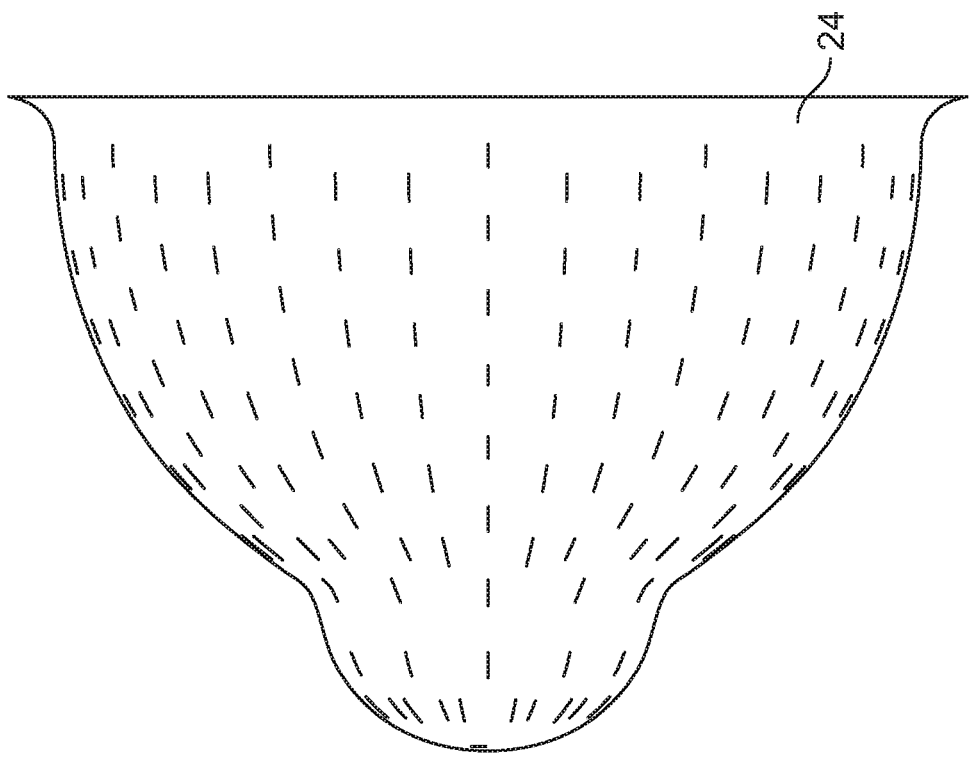

Referring to FIG. 11, a view of the outer layer of the collapsible menstrual cup is shown.

Prior to the layer welds 26 (see FIG. 8), the interior barrier 24 has a simpler shape. It is the welds to create the pockets 36 (see FIG. 8) that create the more complex shape of the final design.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction, and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A menstrual cup comprising:
    an exterior barrier;
    an interior barrier;
    a plurality of absorbent elements placed between the exterior barrier and the interior barrier;
    the exterior barrier affixed to the interior barrier where not separated by the plurality of absorbent elements;
    a rim affixed to the exterior barrier;
    whereby the plurality of absorbent elements absorbs menstrual fluid.

2. The menstrual cup of claim 1, wherein the interior barrier is an impermeable material with openings to allow menstrual fluid to pass through to the plurality of absorbent elements.

3. The menstrual cup of claim 1, wherein the absorbent elements are discrete and unattached to each other.

4. The menstrual cup of claim 1, further comprising:
    a central absorbent element.

5. The menstrual cup of claim 1, wherein the menstrual cup has a first position and a second position:
    the first position being substantially flat, with the interior barrier, exterior barrier, and plurality of absorbent elements fitting substantially within a thickness of the rim; and
    the second position forming a substantially cup-shaped reservoir, with the interior barrier and exterior barrier extending out a bottom of the rim to catch menstrual fluid.

6. A menstrual cup with a collapsed state and an expanded state, the menstrual cup comprising:
    two or more disconnected absorbent elements;
    the two or more disconnected absorbent elements held in position with respect to each other by being sandwiched between an exterior barrier and an interior barrier;
    the collapsed state where the two or more disconnected absorbent elements are in a first position;
    the expanded state where the two or more disconnected absorbent elements are in a second position;
    whereby the disconnected absorbent elements absorb menstrual fluid.

7. The menstrual cup of claim 6, wherein the interior barrier is an impermeable material with openings to allow menstrual fluid to pass through to the disconnected absorbent elements.

8. The menstrual cup of claim 6, further comprising:
    a central absorbent element.

9. The menstrual cup of claim 6, wherein:
    when in the first position, the menstrual cup is substantially flat, with the interior barrier, exterior barrier, and the disconnected of absorbent elements fitting substantially within a thickness of the rim; and
    when in the second position, the menstrual cup is a substantially cup-shaped reservoir, with the interior barrier and exterior barrier extending out a bottom of the rim to catch menstrual fluid.

10. A collapsible menstrual cup comprising:
    an absorbent material;
        the absorbent material divided into two or more discrete and separate elements;
    the absorbent material between an external layer and an internal layer;
        the external layer being impermeable to liquids;
        the interior layer allowing liquids to pass through from an interior to the absorbent material;
    whereby separation of the absorbent material into two or more discrete and separate elements creates a flexible menstrual cup that can be configured into a small collapsed shape.

11. The menstrual cup of claim 10, wherein the internal layer is an impermeable material with openings to allow menstrual fluid to pass through to the discrete absorbent elements.

12. The menstrual cup of claim 10, wherein the two or more discrete and separate elements of absorbent material are unattached to each other.

13. The menstrual cup of claim 10, further comprising:
   a central absorbent element.

14. The menstrual cup of claim 10, wherein the menstrual cup has a first position and a second position:
   the first position being substantially flat, with the internal layer, external layer, and the absorbent material fitting substantially within a thickness of a rim; and
   the second position forming a substantially cup-shaped reservoir, with the internal layer and external layer extending out a bottom of the rim to catch menstrual fluid.

* * * * *